United States Patent [19]

Tarjan et al.

[11] 4,423,732
[45] Jan. 3, 1984

[54] STERILE CONNECTOR SYSTEM FOR PACKAGED PACER

[75] Inventors: Peter P. Tarjan; Marvin L. Sussman, both of Miami, Fla.; Steven Jacobsen, Salt Lake City, Utah

[73] Assignee: Cordis Corporation, Miami, Fla.

[21] Appl. No.: 233,622

[22] Filed: Feb. 12, 1981

[51] Int. Cl.³ .............................................. A61N 1/00
[52] U.S. Cl. .................................................. 128/419 P
[58] Field of Search ...................... 128/419 P, 419 PG; 206/328, 331, 332, 333, 362; 174/50-64

[56] References Cited

U.S. PATENT DOCUMENTS

| 2,856,449 | 10/1958 | Coler | 128/419 P |
| 3,301,392 | 1/1967 | Regan, Jr. | 206/363 |
| 4,026,412 | 5/1977 | Henson | 206/332 |

OTHER PUBLICATIONS

Cordis Publication 149-2340, Rev. O, 1974 15 pages.

Primary Examiner—William E. Kamm
Attorney, Agent, or Firm—Kenway & Jenney

[57] ABSTRACT

A sterile packaging system for an implantable cardiac pacer or tissue stimulator has a ribbon-like electrical connector strip that permits testing and use of the pacer while it remains sealed in a sterile container. The strip is a thin film of a flexible, non-conductive material with a set of longitudinally oriented conductive paths formed on one surface. A nested set of vacuum formed, plastic blister packs surround and secure the pacer. Each blister pack has a removable closure secured to its periphery. The pack and sealant are impervious to biological contaminants. The closure is preferably a film material that is pervious to a sterilizing agent. The connector strip is preferably two strips, each extending through the peripheral seal of one of the packs. The conductive paths of each strip are in series electrical connection when the packs are assembled. A bacteriostatic sealing compound, preferably held in a recess formed in the periphery of each pack over the associated connector strip, blocks biological contamination of the packs along the strips. In the preferred form, the outer end of each connector strip is folded over the recess. The connector strip can include a conductive path that terminates in a large conductive area that is in electrical connection with the case of the pacer. A resilient structure urges the conductive area into a firm contact with the pacer with a minimum of sliding contact between the conductive area of the connector strip and the pacer case.

18 Claims, 7 Drawing Figures

STERILE CONNECTOR SYSTEM FOR PACKAGED PACER

TECHNICAL FIELD

This invention relates in general to packaging systems. More specifically, it relates to a package whose contents can be sterilized and maintained in a sterilized condition and which contains an electrical connector system for using and testing a tissue stimulator without opening the package.

Before a tissue stimulator is implanted in a patient, it is necessary to test the effect of the stimulator, the stimulator itself, and adjust operating parameters of the stimulator such as its rate and pulse amplitude. During these adjustments and testing the stimulator must be maintained in a sterile condition.

BACKGROUND ART

Current practice involves the use of an electronic device, that may be called a "substitution box", to simulate the action of the stimulator. Once a surgeon has secured leads in the tissue, they are connected to the substitution box. For that particular patient and lead implantation, the substitution box aids in the determination of the stimulator's applicability and effectiveness by providing threshold values, that is, minimum voltage or current levels or pulse widths required to obtain the necessary tissue response. These values, obtained from the substitution box, are then used to select, program or adjust the stimulator to be implanted.

The actual implanted stimulator is typically packaged in a disposable container of heavy paper or in double plastic containers. The principal functions of the container or containers are to allow sterilization of the container once it is sealed, to maintain the stimulator in a sterile condition, and to provide protection against physical damage. A conventional form of container opens in a "clamshell" fashion when a covering diaphragm is opened. A sterile stimulator is thus presented for movement into the sterile field of the operating room. Immediately prior to implantation, the stimulator is usually connected to sterilized wires to test its operating condition and then it is connected to a lead or leads of the stimulator connected at one end to the patient's tissue.

This procedure has several drawbacks. First, the substitution box is not identical to the stimulator. Therefore sensitivity and threshold determinations established through the use of the substitution box may not be correct for the stimulator. This is particularly true for establishing stimulus intensity as it can be a complex and delicate procedure. (This may also be true for evaluation of an electrode implant site of the stimulator lead.) Ideally the actual stimulator should be used to make these determinations (and to evaluate the implantation of the leads), but heretofore there has been no way to use the stimulator while it is in its sterile container. Second, if the stimulator is removed from its container and pre-implantation tests indicate that it is defective, the stimulator will no longer be sterile and it must be re-tested, re-packaged and re-sterilized. Since the stimulator is a costly device, there is a strong cost incentive to test the stimulator in a manner which detects a malfunction after sterile packaging but before use in an operation, or to test the stimulator immediately before implantation but without destroying its sterile condition.

While, in general, electrical communication to the interior of a container is known, connection to the interior of a sterile, disposable package for a tissue stimulator presents special problems. The electrical connection must penetrate the package while at the same time not allowing bacteria or other biological contaminants to penetrate the package and destroy its sterility or alter its contents. Further, the electrical connection must not even reduce the reliability of the package in maintaining a sterile interior. With stimulator packaging these opposed objectives are complicated by the fact that the electrical conductors must carry a current strong enough to produce the desired tissue response, there must be multiple electrical paths through the package, and the bacterial seal must not be broken by mechanical stresses encountered in normal handling and the connection of other electrical circuitry to the conductors.

A further requirement peculiar to stimulator packaging is that certain stimulators utilize the outer metallic case of the stimulator as a reference voltage ground. The connector system must therefore make electrical connection to the case. However, the connection cannot involve a scraping contact between the connector and the case. During any such metal-to-metal scraping, some trace quantity of one metal, usually the softer metal forming the connector, deposits on the case. When this stimulator is implanted, body fluids begin a galvanic process which corrodes the case. Since a stimulator is usually implanted for many years of uninterrupted service, corrosion is a serious problem and must be prevented.

It is therefore a principal object of this invention to provide a connector system for a sealed package that provides electrical communication with the sterile interior of the packaging without compromising its sterility.

Another object of this invention is to provide a sterile connector system for a tissue stimulator package that allows the stimulator to be tested and allows the performance of pre-implantation tests without removing it from its sterile packaging.

Yet another object of this invention is to eliminate the use of a substitution box and to ensure that threshold and sensitivity values determined prior to implantation are accurate.

A further object is to provide a sterile connection and packaging system for a stimulator that makes reliable electrical connection to the case of the stimulator without scratching the case or otherwise promoting the corrosion of the case through galvanic reactions once the stimulator is implanted.

A still further object of the invention is to improve quality control for implantable stimulators.

Another object is to provide a sterile packaging system which allows a visual inspection of the stimulator in a package and allows the introduction of a sterilizing agent.

Yet another object is to provide a sterile connector for a packaged stimulator that is highly reliable and has a relatively low cost of manufacture.

SUMMARY OF THE INVENTION

This invention provides a sterile electrical connector system between the sterile interior of a sealed package and its exterior. The invention is particularly useful in packaging implantable tissue stimulators such as cardiac pacers. The pacer can be held in a single package, but is preferably held in a sealed inner "pack" which in turn is nested within a sealed outer "pack". Each pack is formed of a material or materials that are impervious to biological contaminants. Each pack also has a detachably sealed portion, preferably a bottom wall, that provides access to the interior of the pack. The bottom wall is sealed to the pack, preferably along a common periphery, by a material that is also impervious to biological contaminants. In the preferred form, the packs are formed principally of a clear, vacuum molded plastic material such as polyvinyl chloride. The bottom wall or closure is a film that is permeable to a sterilizing agent such as ethylene oxide. A polyolefin film coated with a conventional sealing material that bonds the film to the pack under the application of heat and pressure is recommended.

A ribbon-like electrical connector strip, and preferably a pair of such strips each associated with one of the packs, provides the electrical communication to the interior of the sterile package. Each strip is formed from a film material that is strong, flexible, and non-conductive. Any of a wide range of such plastic materials is suitable. A recommended material is the product sold by I. E. DuPont deNemours Company under the trade designation Kapton. At least two and usually three longitudinally extending conductive paths are formed on one surface of the strip. The conductive paths are extremely thin, but wide enough to provide a sufficient cross-sectional area to carry the usual output current of the pacer. In the preferred form, with copper or a copper alloy as the conductive material, the paths each have a thickness of approximately 1 mil and a width of approximately ⅛ inch. The supporting plastic film substrate is also thin, with a typical thickness being 2 mils.

The strips each extend through the peripheral seal between the blister pack and the detachable closure. One end of the strip is located within the associated pack and the other end projects from the pack. A bacteriostatic sealing compound secures the strips, particularly their side edges, to the surrounding components of the pack while blocking the passage of biological contaminants into the packs along the strips. Each blister pack preferably has a recess formed in it periphery which holds a supply of the bacteriostatic compound. The sealing compound must be sufficiently viscous to flow around the connector strips when the pack is assembled. It must also (1) provide a good bond to the materials forming the packs and the strips, (2) exhibit a sufficient amount of flexibility to accommodate flexures and other mechanical strains on the packaging, particularly around the connector strips, and (3) maintain its mechanical, adhesive and bacteriostatic properties over the life of the package.

When two packs and two associated connector strips are used, the connector strips each have their "exterior" end folded over the raised side of the recess. The corresponding conductive paths of the strips are in face-to-face electrical contact over the recess of the inner pack. This recess acts as a spring that urges the conductive paths into contact with one another. At the outer pack recess, the folded configuration presents the conductive paths on the "outer" strip for connection to an external connection harness.

Where the pacer circuitry is grounded to the pacer's outer case, the connector strip has one conductive path that terminates at the interior of the inner pack in a broad area contact "pad". In the preferred form, the pad is an enlarged end portion of the connector strip. The conductive area of the pad is positioned opposite one face of the metallic outer case of the pacer. The pad can also be a carbon loaded silicone member with an imbedded wire mesh. The connector system preferably includes an arrangement for applying a positive contact force between the case and the pad. One arrangement is a snap on clamp that holds the pad against the case. Another arrangement is a series of ribs formed in the blister portion of the inner packs adjacent the pacer which apply a spring force on the pacer when the pack is sealed. Alternatively a non-scraping contact force can be generated by a foam pad or a partial vacuum within the inner pack.

These and other features and objects of the present invention will become apparent from the following detailed description which should be read in light of the accompanying drawings.

DETAILED DESCRIPTION OF THE PREFERRED EMBODIMENTS

Figure 1:
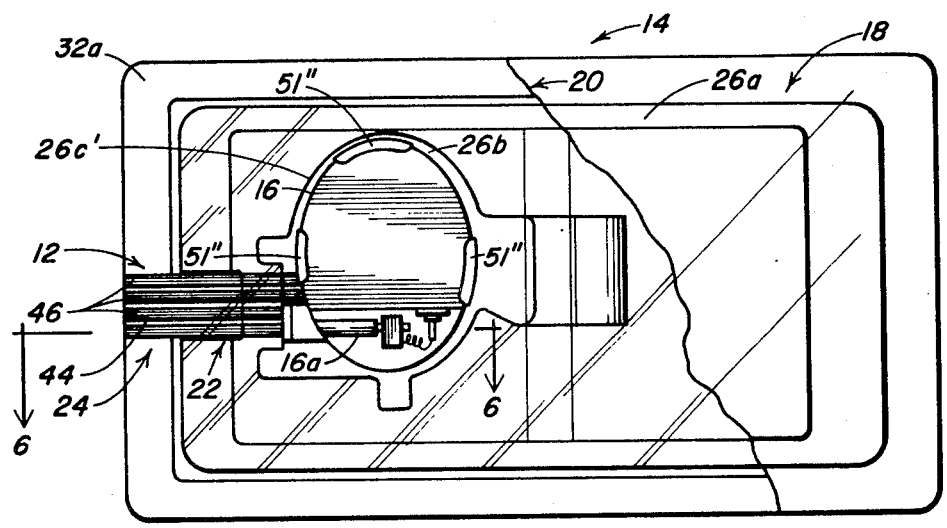
FIG. 1 is a top plan view with portions broken away of a sterile connector and pacer packaging system according to the present invention.
Figure 2:
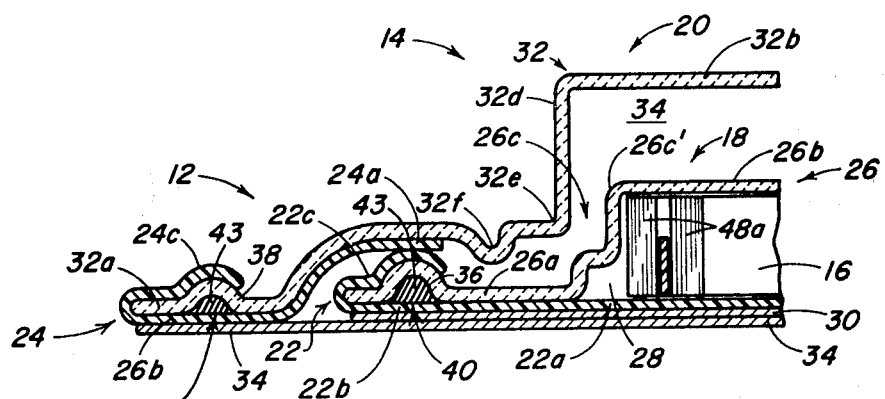
FIG. 2 is a detailed view in vertical section of the sterile connector system shown in FIG. 1 taken along the line 2—2.

FIGS. 1 and 2 show a sterile connector system 12 according to this invention that provides electrical communication between the exterior and interior of a packaging system 14 adapted to hold a tissue stimulator, in this case an implantable cardiac pacer 16. The pacer 16 can be any one of the wide variety of pacers presently on the market including programmable, non-programmable, unipolar and bipolar pacers. The pacer 16 illustrated in the drawings is a unipolar, programmable pacer sold by the Cordis Corporation of Miami, Fla. under the trade designation Omni Stanicor (Gamma).

Figure 3:
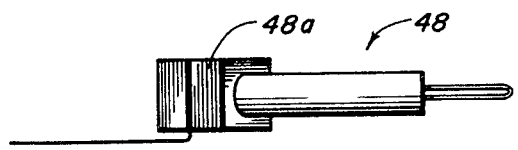
FIG. 3 is a view in side elevation of the connector jack shown in FIGS. 1 and 2.
Figure 4:
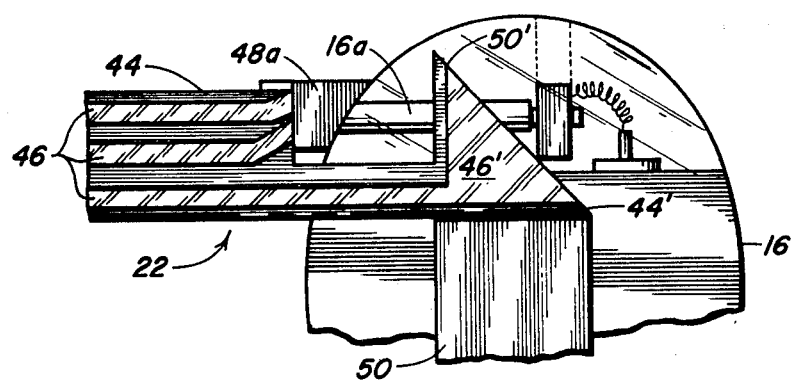
FIG. 4 is a detailed rear plan view of the sterile connector system shown in FIGS. 1 and 2 with portions broken away and with particular reference to the electrical connection of the connector strip to the pacer.
Figure 5:
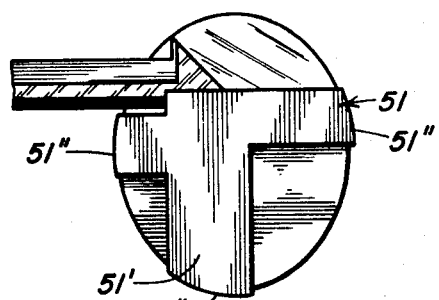
FIG. 5 is a view corresponding to FIG. 4 showing a resilient clip that secures the pad portion of the connector strip to the case of the pacer.
Figure 6A:
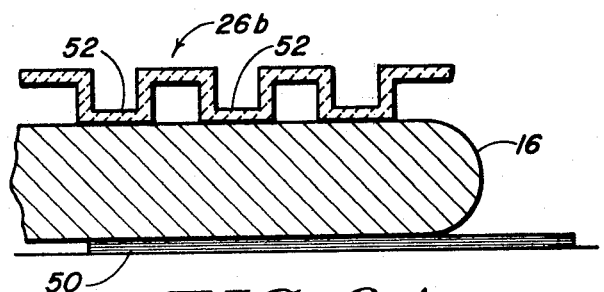
FIGS. 6a and 6b are detailed views of an alternative arrangement for urging the pad into electrical connection with the pacer.
Figure 6B:
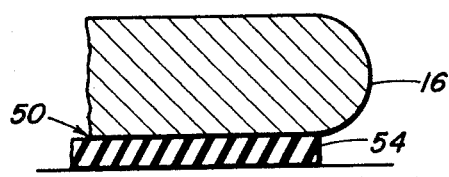

Electrical connection to the pacer is made through a passageway 16a oriented toward the side of the pacer and located at its upper end. A connecting jack 48 is inserted into the passageway to make electrical connection to the pacer. The jack, shown in detail in FIG. 3, is preferably of a conventional "banana clip" design terminated at the exterior of the pacer in a connection block 48a. The jack can have one, two, three or more separate conductors. With certain pacers, the metallic outer case of the pacer is electrically connected to the electronic circuit contained within the pacer and serves as a ground. For these pacers, it is necessary to have a separate electrical connection to the metallic outer case of the pacer.

In the preferred form illustrated, the packaging system 14 consists of an inner pack 18, an outer pack 20 that surrounds the inner pack, and the sterile connector system 12 which extends through the peripheries of both the inner and outer packs to provide a continuous electrical connection between the exterior of the outer pack 20 and the interior of the inner pack 18. A significant feature of this invention is that the connector system utilizes a flat, ribbon-like connector, and preferably a pair of such connector strips 22 and 24 associated with the inner and outer packs 18 and 20, respectively. Each strip has an inner portion 22a, 24a that lies within the interior of the associated pack, an intermediate portion 22b, 24b secured in the periphery of the packs, and an exterior portion 22c, 24c.

The inner pack 18 has an "upper" wall portion 26 that includes a generally flat periphery 26a and at least one portion 26b which is spaced vertically from the peripheral portion 26a to define an interior compartment 28 of the pack 18. The portion 26b is connected continuously to the periphery 26a by a side wall portion 26c. The entire wall 26 is formed of a material which is impervious to the passage of biological contaminants and is therefore capable of maintaining a sterile condition at the interior 28 of the pack. The wall 26 is also preferably formed of a transparent material that is readily molded by conventional vacuum forming techniques. A suitable material is polyvinyl chloride. The transparency of the wall 26 allows a visual inspection of the pacer 16 within the pack 18 to read identifying information etched on the exterior of the pacer. This material also does not interfere with electromagnetic signals which may be used to transmit signals to the pacer that control its programming.

The inner pack 18 preferably has its wall portion 26b in direct contact with the upper face of the pacer 16. An adjoining curved section 26c' of the wall portion 26c conforms to the curved edge of the pacer 16. This curved section 26c' and the wall portion 26b form a "depression" or receptacle that corresponds to the shape of the pacer to firmly locate it within the inner pack. Typically hardware associated with the pacer is also held in like receptacles (not shown) formed in the upper wall 26. A plastic walled package with such receptacles is commonly referred to as a "blister" pack.

The second major component of the inner pack 18 is a "bottom" wall 30 which has a generally planar configuration and is substantially coextensive with the upper wall 26. The bottom wall 30 is preferably formed of a film material which is impervious to biological contaminants but which passes a sterilizing agent such as ethylene oxide. In addition, the film 30 has a coating of an adhesive material which causes it to bond to the material forming the upper wall 26 under the application of heat and pressure. A suitable material for the wall 30 is a coated polyolefin film sold under the trade designation Tyvek. The wall 30 is bonded to the peripheral portion 26a to provide a continuous seal around the periphery of the pack between the members and 26 and 30 (with the possible exception of the area around the connector strip 22) and thereby form a closed, sealed pack that can be sterilized and maintain a sterile interior indefinitely. The seal, however, can be broken manually by separating the wall 30 from the periphery 26a.

The outer pack 20 has generally the same construction as the inner pack 18. An upper "blister" wall 32 is formed of a material having the same characteristics as the upper wall 26. It also has a generally flat peripheral portion 32a, a "raised" portion 32b which defines an interior holding area or compartment 34 of the pack. As noted above, the wall 32 is configured to secure the inner pack and a nested relation with respect to the outer pack. A bottom wall 34 of the outer pack 20 is formed of the same material as the bottom wall portion 30. It also is sealed at its periphery to the periphery 32a of the upper wall 32. The peripheral seal between the members 32 and 34, together with the walls 32 and 34, block the passage of biological contaminants from the exterior of the pack 20 to its interior chamber 34 (with the possible exception of the region surrounding the connector strip 24).

As is best seen in FIG. 2, the upper wall 32 includes a vertical side wall portion 32d which terminates adjacent the pacer 16 in a corner 32e. This corner 32e extends around the "highest" portions of the upper wall 26 and thereby physically limits the movement of the inner pack 18 within the outer pack 20. In addition, the blister portion 32 has a downwardly projecting recess 32f which also limits the movement of the pack 18 within the pack 20 and provides a positive "snap in" engagement between the packs when they are assembled.

The packs 18 and 20 each include a recess, 36 and 38 respectively, in their peripheries at a point that overlies the intermediate portions 22b and 24b of the associated connector strips. Each recess 36, 38 extends generally transversely to the connector strips for a distance at least equal to the width of the strip. The recesses are also approximately centered on the peripheral portion of the associated blister pack measured on a perpendicular to the edge.

These recesses define clearances 40 and 42 that hold a supply of a bacteriostatic sealing compound 43 such as a bacteriostatic silicone rubber material sold by the Dow Chemical Company under the trade designation Silastic. When the packs 18 and 20 are assembled, the sealing compound 43 held in the clearances 40 and 42 flows around the connector strips, and in particular the side edges of the connector strips, to provide a reliable, continuous seal that blocks the passage of bacteria or other organic contaminants along the connector strip to the interior of the packs 20 and 18. The sealing compound must form a reliable bond to the materials forming the walls of the packs 18 and 20 as well as the connector strips 22 and 24. It must also be flexible once the seal is established to accommodate flexures of the packs in normal use, or other mechanical stresses, without rupturing the seal. Another quality of the sealing compound is that it should maintain its mechanical, adhesive and bacteriostatic characteristics over the expected life of the packaging system 14.

The connector strips 22 and 24 each include a thin, yet strong substrate 44. The substrate is also flexible, electrically nonconductive, and formed of a material which bonds effectively to the materials forming the packs 18 and 20. A recommended material is a 2 mil film of the product sold by DuPont under the trade designation Kapton. Each strip 22 and 24 also includes a set of longitudinally extending, parallel conductive paths 46 deposited on the substrate 44 by conventional techniques. The paths 46 are preferably formed of copper or a copper alloy. While the conductive paths are extremely thin, a typical thickness being 1 mil, they can carry the output currents of the pacer 16 due to the comparatively large width of each path 46. For example, conductive paths with a width of $\frac{1}{8}$ inch can carry a typical pacer output current of 4 to 10 milliamps. Each path 46 is separated by a region which contains no conductive material and therefore the paths are electrically isolated from one another.

A principal advantage of the present invention is that by utilizing strips having this construction, it is possible to seal the strips between the walls 26 and the wall 30, or in the case of the outer pack between the wall 32 and the bottom wall 34, in a manner which provides a strong and reliable seal. Another advantage to this configuration is that the conductive paths remain mutually aligned and insulated from one another. Further, the construction of the connector strips and the packs results in a seal between these members which retains its integrity with a high degree of reliability under the mechanical stresses commonly associated with assembling, handling and using the packaging system 14.

The inner connector strip 22 associated with the inner pack 18 is oriented with the connector strips facing downwardly, that is, toward the bottom wall 30. When the outer end 22c of the strip is folded over the raised side of the recess 36, the connector paths 46 face upwardly. The conductive paths 46 are connected to the pacer 16 at the inner end 22a through the plugin jack 48. The connection block 48a of the jack 48 exterior to the pacer is secured to the end 22a and electrical conductors of the jack are secured to appropriate ones of the paths 46.

The outer connector strip 24 has the same orientation as the strip 22. Moreover, the connector strips 22 and 24 are aligned with their respective conductive paths 46 in a face-to-face electrical connection, at the end 22c and the end 22a. This establishes a series electrical connection between the paths 46 on the strips 22 and 24. The recess 36, acting in combination with the bottom walls 30 and 34 and the outer pack portion 32f directly overlying the inner end 24a, urges the connector strip ends 22c and 24a toward one another to establish a reliable electrical connection. The outer end 24c is also folded over the peripheral portion of the outer pack 20, and in particular the raised side of the recess 38, so that the conductive paths 46 are upwardly facing and presented for connection to an external connection harness. It should be noted that this construction greatly reduces the likelihood of damage to the exterior ends of the conductors as compared, for example, to a system using a set of ordinary wires with no common support element.

FIGS. 4–6b demonstrate in detail the connector system 12 of this invention where in addition to the pacer connection through the jack 48, the connector system has an additional electrical path which terminates in a large area pad 50 which is in contact with one face of the outer metallic case of the pacer 16. In the preferred form illustrated, the pad 50 is simply an extension of the connector strip 22 which has a configuration and location adapted to mate with the lower face of the pacer 16 when it is positioned in its holding receptacle in the inner pack 18. The pad includes a continuation 44' of the substrate 44 and a large area deposit 46' of the conductive material forming the paths 46. Since the paths 46 face downwardly and the pad area 46' must face upwardly, the pad is folded over (along the line 50' in FIG. 4) with respect to the remainder of the strip 22.

Because the metallic case of the pacer is typically made of a comparitively hard metal such as titanium and the material forming the electrically conductive area of the pad 50 is a comparatively soft metal, any sliding movement between the pad and the pacer case will result in at least trace quantities of the softer metal being abraded and deposited on the surface of the case of the pacer. When the pacer is implanted in the patient, these deposits form small galvanic cells which corrode of the case of the pacer. It is therefore most important that the case be positioned on the pad and a reliable electrical connection established between the pad and the case with no sliding movement. One arrangment for ensuring a good electrical connection is to apply a spring force in the direction normal to the interface between the pacer case and the conductive pad 50. In the preferred form shown, the spring force is developed by a clip 51 (FIGS. 2 and 5) that snaps onto the sides of the pacer. The rear surface 51' of the clip is enlarged and presses the pad 50 against the case. Three C-shaped portions 51'' engage the edge of the pacer at its sides and bottom and together with the portion 51' secure the clip 51 to the pacer and develop the desired spring force. In another form, a series of ribs 52 (FIG. 6a) formed in the wall portion 26b of the inner pack at a point directly overlying the pacer develop the spring force. When the pacer is secured in the inner pack 18, the ribs are deflected slightly so that their inherent resiliency of the plastic material forming the wall 26b and the ribs 52 generates the desired downward contact force. Other alternative arrangements include the provision of a resilient pad 54 (FIG. 6b) under the electrical connection pad 50 and a vacuum in the interior compartment 28 of the inner pack 18 which causes the walls of the pack to collapse toward one another. It should also be noted that the pad 50 can assume other forms, for example, a carbon-loaded silicone rubber pad with or without a wire mesh embedded in the pad that makes the desired electrical connection to the pacer case.

There has been described a sterile connector system for a packaged pacer which allows the testing and use of a pacer 16 in an operating room prior to implantation without removing the pacer from its sterile packaging. The system is reliable, simple to use, and results in more accurate settings of operating parameters for the pacer once it is implanted. All of these objectives are achieved through a relatively simple construction which has a comparatively low cost of manufacture.

Further, while the invention has been described in its preferred embodiment, that is, for use in connection with a cardiac pacer and a double nested set of packs 18 and 20, it is also possible to utilize a single pack and a single connector strip. The main disadvantage of the single pack is that there is only one set of barriers to biological contaminants in the pacer rather than two. Of course, it is possible to further enclose either a single pack or a nested double pack in a conventional heavy paper package which can provide yet another barrier to biological contamination. If a double pack is used, with or without an outer paper package, the outer pack can be opened to transfer the inner pack to the sterile field. If the implant is aborted at this point, the inner pack will maintain the pacer in a sterile condition.

Another possible alternative construction involves the use of packs which have different configurations and different modes of sealing. For example, a single pack can be formed in two portions that mate in an overlapping or telescoping fashion with overlapping region sealed by an adhesive strip or a sealing material located between the overlapping portions. Still another alternative is forming the component walls of a pack of the same material in contrast to the preferred embodiment where the "upper" wall 26, for example, is of a different material than the "lower" wall 30.

These and other variations and modifications will occur to those skilled in the art from the foregoing detailed description and the accompanying drawings. Such modifications and variations are intended to fall within the scope of the appended claims.

What is claimed and desired to be secured by Letters Patent is:

1. A connector system that transmits tissue stimulating electrical signals and bioelectric signals from the tissue to the packaged device between the interior and exterior of a closed packaging system having first and second wall members detachably sealed at a common periphery comprising, a flat, elongated connector strip having a first end location within the interior of the packaging system, a second end exterior to the packaging system and an intermediate portion disposed in the sealed peripheral region between said first and second wall members, said connector strip having a flexible, non-conductive substrate and at least one thin, longitudinally extending layer of a conductive material secured on and projecting from at least one surface of said substrate, and means for sealing said substrate, including its side surfaces and said conductive path, to said first and second wall members, said sealing means being capable of maintaining said seals during mechanical stresses on said connector strips and the surrounding portions of said first and second wall members, said sealing means comprising an adhesive material held in a recess formed in one of said first or second wall members adjacent said intermediate portion of said strip and adapted to hold and disperse said adhesive material.

2. A connector system according to claim 1 wherein said adhesive material is bacteriostatic.

3. A connector system according to claim 2 wherein said sealing means has a viscosity that allows it to flow around said connector strip to at least the sides of said strip.

4. A connector system according to claim 3 wherein said second strip end exterior to said packaging system is folded over the raised side of said recess.

5. A connector system according to claim 1 wherein said package holds a cardiac pacer and wherein said connector strip includes a pad portion at said first end that is in face-to-face contact with the outer case of said pacer.

6. A connector system according to claim 5 further comprising means for resiliently urging said pad portion and said pacer case against one another.

7. A connector system according to claim 6 wherein said resilient means comprises a spring clip secure to said pacer.

8. A connector system according to claim 7 wherein said resilient means comprises ribs formed in one of said first and second wall members which is itself formed of a resilient sheet material.

9. A sterile packaging system with intrusive electrical communication to the interior of the system comprising,
an inner package defining a sterilizable interior compartment and having a first detachable member to open said inner package,
an outer package defining a sterilizable interior compartment that holds said inner package, said outer package having a second detachable member to open said outer package,
means for sealing said first and second detachable members to said inner and outer packages, respectively, said sealing means and said inner and outer packages including said first and second detachable members being impervious to biological material when said detachable members are thus sealed to close said inner and outer packages,
first and second strips of a flexible, non-conductive material with at least one longitudinal conductive path formed on and projecting from at least one surface of each strip, said first strip being associated with said inner package and said second strip being associated with said outer package, said first and second strips extending from said interior compartments of both of said inner and outer packages, respectively, to the exterior of said outer package, said first and second strips passing between adjacent, sealed portions of said detachable members and said packages, and
means for sealing said first and second strips against biological contamination of said compartments said strip sealing means comprising a bacteriostatic sealing compound held in flexible recesses formed in a peripheral portion of said packages adjacent said first and second strips, said sealing compound being sufficiently flexible to maintain said seal during mechanical stresses applied to said packaging system around said connector strips.

10. A sterile packaging system according to claim 9 wherein said first and second strips each have a first end extending into the interior compartment of the associated package and a second end extending outside of said associated package.

11. A sterile packaging system according to claim 10 wherein said second end of said first strip and said first end of said second strip are in series electrical connection when said inner package is secured in said outer package.

12. A sterile packaging system according to claim 11 wherein said inner and outer packages each have a flexible recess formed in a peripheral portion of said packages adjacent said associated strip and further comprising bacteriostatic sealing compound held in said recess that bonds said electrical connection means to said inner and outer packages.

13. A sterile packaging system according to claim 11 wherein said second ends of said first and second strips are folded back to overlie the raised outer surface of the associated ones of said recesses.

14. A sterile packaging system according to claim 9 wherein said inner and outer packages each include an upper portion having a substantially flat periphery and central portion that defines said compartment and said detachable member comprises a substantially flat lower portion.

15. A sterile packaging system according to claim 14 wherein said upper portion is a clear plastic material.

16. A sterile packaging system according to claim 14 wherein said detachable portion comprises a sheet of a material that is impervious to biological material while being pervious to a sterilizing agent.

17. A sterile packaging system according to claim 16 wherein said sheet material is a polyolefin film and said sealing means comprises a coating on said polyolefin film that adheres to said film and to the periphery of said upper package portions when subjected to heat and pressure.

18. A sterile packaging system according to claim 12 wherein said sealing compound has a sufficient viscosity to flow around said connector strips from said recesses to at least the sides of said strips.

* * * * *